(12) United States Patent
Ponsky et al.

(10) Patent No.: US 9,750,621 B2
(45) Date of Patent: Sep. 5, 2017

(54) URETERAL STENT FOR PLACEMENT IN A KIDNEY AND BLADDER

(71) Applicant: University Hospitals Health System, INC., Cleveland, OH (US)

(72) Inventors: Lee E. Ponsky, Moreland Hills, OH (US); Dean Secrest, Concord, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 10 days.

(21) Appl. No.: 14/406,392

(22) PCT Filed: Jun. 10, 2013

(86) PCT No.: PCT/US2013/044972
§ 371 (c)(1),
(2) Date: Dec. 8, 2014

(87) PCT Pub. No.: WO2013/185128
PCT Pub. Date: Dec. 12, 2013

(65) Prior Publication Data
US 2015/0142127 A1    May 21, 2015

Related U.S. Application Data

(60) Provisional application No. 61/657,228, filed on Jun. 8, 2012.

(51) Int. Cl.
*A61F 2/04*       (2013.01)
*A61F 2/82*       (2013.01)
*A61M 27/00*   (2006.01)

(52) U.S. Cl.
CPC ............. *A61F 2/82* (2013.01); *A61M 27/008* (2013.01); *A61F 2002/047* (2013.01);
(Continued)

(58) Field of Classification Search
CPC .......... A61F 2002/047; A61F 2002/048; A61F 2220/0075; A61F 2002/067; A61F 13/34;
(Continued)

(56) References Cited

U.S. PATENT DOCUMENTS 3,995,642 A * 12/1976 Adair ................... A61M 25/00
                                                                          604/544
4,787,884 A * 11/1988 Goldberg .......................... 604/8
(Continued)

FOREIGN PATENT DOCUMENTS

| AT | DE 4103573 A1 * 8/1992 | .......... A61M 27/008 |
|---|---|---|
| DE | 4134030 C2 * 4/1997 | .......... A61M 27/008 |

(Continued)

OTHER PUBLICATIONS

International Search Report and Written Opinion for corresponding Patent Application No. PCT/US2013/044972 dated Aug. 27, 2013.

*Primary Examiner* — Andrew Iwamaye
(74) *Attorney, Agent, or Firm* — Tucker Ellis LLP; Patrick F. Clunk (57) ABSTRACT

Provided is a ureteral stent (=50) including a bladder portion (=52) positioned in a bladder of a patient, a kidney portion (=54) positioned in a kidney and ureteral passageway of the patient, and one or more tethers (=56) coupling the bladder portion to the kidney portion. The ureteral stent allows urine to pass around a blockage, and allows a ureter orifice connecting the ureteral passageway to the bladder to move between a compressed state and an uncompressed state to prevent or minimize urinary reflux, flank pain, blood in the urine, etc., while allowing the bladder portion to move freely in the bladder to prevent the bladder portion from irritating the trigone muscle.

16 Claims, 9 Drawing Sheets

(52) U.S. Cl.
CPC ... *A61F 2002/048* (2013.01); *A61F 2220/005* (2013.01); *A61F 2220/0008* (2013.01); *A61F 2220/0075* (2013.01); *A61F 2230/0006* (2013.01); *A61F 2230/0013* (2013.01); *A61F 2230/0041* (2013.01); *A61F 2230/0069* (2013.01); *A61F 2250/0006* (2013.01); *A61F 2250/006* (2013.01); *A61F 2250/0014* (2013.01); *A61F 2250/0018* (2013.01); *A61F 2250/0019* (2013.01); *A61F 2250/0029* (2013.01); *A61F 2250/0036* (2013.01); *A61F 2250/0039* (2013.01); *A61F 2250/0098* (2013.01)

(58) Field of Classification Search
CPC .................. A61F 13/204; A61F 13/208; A61F 2002/9155; A61F 2002/91558; A61F 2002/91566; A61F 2002/91575; A61F 2002/915835; A61F 2002/828; A61F 2002/826; A61M 27/008
See application file for complete search history.

(56) References Cited

U.S. PATENT DOCUMENTS

| | | | | |
|---|---|---|---|---|
| 4,790,809 | A | * | 12/1988 | Kuntz .................. 604/8 |
| 4,874,360 | A | * | 10/1989 | Goldberg et al. .................. 604/8 |
| 4,913,683 | A | | 4/1990 | Gregory |
| 4,931,037 | A | | 6/1990 | Wetterman |
| 5,141,502 | A | | 8/1992 | Macaluso |
| 5,322,501 | A | | 6/1994 | Mahmud-Durrani |
| 5,456,246 | A | * | 10/1995 | Schmieding ........... A61B 17/02 600/201 |
| 5,599,291 | A | * | 2/1997 | Balbierz et al. ................. 604/8 |
| 6,258,098 | B1 | | 7/2001 | Taylor |
| 6,652,569 | B1 | * | 11/2003 | Taylor ...................... A61F 2/04 606/108 |
| 6,656,146 | B1 | * | 12/2003 | Clayman et al. ................. 604/8 |
| 6,852,105 | B2 | * | 2/2005 | Bolmsjo et al. ............. 604/544 |
| 7,041,139 | B2 | | 5/2006 | Bluni |
| 8,070,825 | B2 | * | 12/2011 | Devonec .................... 623/23.7 |
| 8,474,814 | B2 | * | 7/2013 | Noda et al. ................... 271/227 |
| 9,492,266 | B2 | * | 11/2016 | Hutchins, III .... A61M 25/0017 |
| 2002/0143389 | A1 | * | 10/2002 | St. Pierre .......... A61M 25/0009 623/1.15 |
| 2003/0109930 | A1 | * | 6/2003 | Bluni et al. .................. 623/23.7 |
| 2003/0153973 | A1 | * | 8/2003 | Soun ........................ A61F 2/90 623/1.16 |
| 2003/0176912 | A1 | * | 9/2003 | Chuter ...................... A61F 2/07 623/1.13 |
| 2003/0181842 | A1 | * | 9/2003 | Gellman ........................... 604/8 |
| 2004/0059279 | A1 | * | 3/2004 | McWeeney et al. ............. 604/8 |
| 2004/0167635 | A1 | * | 8/2004 | Yachia ...................... A61F 2/90 623/23.66 |
| 2005/0149201 | A1 | * | 7/2005 | McWeeney et al. ...... 623/23.68 |
| 2006/0052815 | A1 | * | 3/2006 | Fitz ................... A61B 17/0057 606/200 |
| 2007/0293929 | A1 | * | 12/2007 | Aoba ....................... A61F 2/95 623/1.11 |
| 2008/0004578 | A1 | * | 1/2008 | Hixon et al. .................. 604/326 |
| 2008/0077250 | A1 | * | 3/2008 | Amos ....................... 623/23.66 |
| 2008/0183299 | A1 | * | 7/2008 | Monga et al. ............. 623/23.66 |
| 2009/0163780 | A1 | * | 6/2009 | Tieu ................. A61B 17/12022 600/301 |
| 2010/0070024 | A1 | * | 3/2010 | Venturelli ................. A61F 2/90 623/1.22 |
| 2010/0152861 | A1 | * | 6/2010 | Chung ...................... A61F 2/04 623/23.7 |
| 2010/0160848 | A1 | * | 6/2010 | Ostrovsky et al. ............... 604/8 |
| 2010/0324540 | A1 | * | 12/2010 | Paulen et al. ................. 604/544 |
| 2011/0320008 | A1 | | 12/2011 | Teague et al. |
| 2012/0158155 | A1 | * | 6/2012 | Shin ........................ A61F 2/04 623/23.66 |
| 2012/0303109 | A1 | * | 11/2012 | Okuma ..................... A61F 2/95 623/1.11 |
| 2013/0158675 | A1 | * | 6/2013 | Hutchins, III .... A61M 25/0017 623/23.66 |

FOREIGN PATENT DOCUMENTS

| | | | |
|---|---|---|---|
| FR | 2577809 A1 | * 8/1986 | ............... A61F 2/04 |
| WO | 2005/096991 | 10/2005 | |
| WO | WO 2005102217 A1 | * 11/2005 | |
| WO | WO 2007001978 A2 | * 1/2007 | |

* cited by examiner

URETERAL STENT FOR PLACEMENT IN A KIDNEY AND BLADDER

RELATED APPLICATIONS

This application is a national phase of International Application No. PCT/US2013/044972 filed on Jun. 10, 2013 and published in the English language, which claims the benefit of U.S. Provisional Application No. 61/657,228 filed Jun. 8, 2012, which is hereby incorporated herein by reference.

FIELD OF INVENTION

The present invention relates generally to implantable medical devices, and more particularly to stents, such as ureteral stents.

BACKGROUND

The urinary tract has a pair of kidneys that connect to a bladder by ureteral passageways, and a urethra that extends from the bladder to the exterior of a patient. Urine is made by the kidneys, passed through the ureteral passageway, stored in the bladder and ultimately voided from the urethra. A urinary sphincter is positioned around the urethra near the base of the bladder to control the flow of urine from the bladder.

The ureteral passageways normally allow urine to pass from the kidney to the bladder by peristalsis. When the bladder fills with urine, the bladder compresses a segment of the ureteral passageway that passes through a wall of the bladder to prevent urine from going backwards from the bladder into the kidney. These passageways can become blocked by tumors or kidney stones thereby preventing normal urine flow, and the resulting high pressure within the kidneys can cause pain to the patient. To reopen a blocked ureteral passageway, a ureteral stent can be positioned in the patient. The stent holds the blockage in the passageway open, for example to allow a small kidney stone to pass. This enables urine to flow from the kidney into the bladder, reduces kidney pressure, and reduces pain of the patient.

SUMMARY OF INVENTION

The present invention provides a ureteral stent including a bladder portion positioned in a bladder of a patient, a kidney portion positioned in a kidney and ureteral passageway of the patient, and one or more tethers coupling the bladder portion to the kidney portion. The ureteral stent allows urine to pass around a blockage, and allows a ureter orifice connecting the ureteral passageway to the bladder to move between a compressed state and an uncompressed state to prevent or minimize urinary reflux, flank pain, blood in the urine, etc., while allowing the bladder portion to move freely in the bladder to prevent the bladder portion from irritating the trigone muscle.

According to one aspect of the invention, a ureteral stent for placement in a bladder, a kidney and a ureteral passageway connecting the bladder and kidney is provided. The ureteral stent includes a bladder portion configured to be positioned in the bladder, the bladder portion being resilient and biased in an unrestrained position to prevent the bladder portion from migrating into the ureteral passageway when positioned in the bladder, a kidney portion configured to be positioned in the kidney and the ureteral passageway, the kidney portion having a ureter portion configured to be positioned in the kidney and the ureteral passageway to place the ureteral passageway in an open state and a resilient fixing portion biased in an unrestrained position to secure the resilient fixing portion in the kidney when positioned in the kidney, and at least one tether coupled to the bladder portion and the ureter portion to allow the bladder portion to float in the bladder and to allow a ureter orifice connecting the ureteral passageway to the bladder to move between a compressed state and an uncompressed state.

The bladder portion and the fixing portion are movable between a restrained position when being positioned in the bladder and kidney, respectively, and the unrestrained position when positioned in the bladder and kidney, respectively.

The bladder portion and kidney portion are substantially straight when in the restrained position and curved when in the unrestrained position.

The bladder portion and kidney portion each include at least one radiopaque element on outer surfaces thereof to assist an operator in positioning the stent.

The bladder portion and kidney portion have first and second ends, respectively, each end having at least one radiopaque element.

The bladder portion and ureter portion of the kidney portion each include a least one opening in a wall thereof providing a passage between an outside of the bladder and kidney portions and an inside of the bladder and kidney portions for receiving the tether.

The tether extends from the inside of the bladder and kidney portions to the outside of the bladder portions, and wherein the tether has a first end and a second end coupled together outside the bladder and kidney portions forming a coupled tether portion.

The ureteral stent further includes sleeve coupled to the wall of the bladder portion adjacent the opening in the wall, the sleeve covering the coupled tether portion.

The bladder portion includes a tip at a first end opposite a second end coupled to the tether, the tip having a stiffness greater than a stiffness of the bladder portion.

The tether is a suture.

The bladder portion, kidney portion and tether are formed from an extruded tubular member.

A section of the tubular member is removed to form the tether.

The bladder portion is a flexible loop when in the unrestrained position.

The bladder portion is J-shaped when in the unrestrained position.

The bladder portion is helical when in the unrestrained position.

The fixing portion is a flexible loop in the unrestrained position.

The fixing portion is J-shaped in the unrestrained position.

The fixing portion is helical when in the unrestrained position.

The bladder portion and kidney portion each include a least one opening in a wall thereof providing a fluid passage between an outside of the bladder and kidney portions and an inside of the bladder and kidney portions.

The kidney portion has a durometer between about 50 shore A and about 80 shore A.

The resilient fixing portion has a durometer greater than a durometer of the ureter portion.

The bladder portion has a durometer between about 25 shore A and about 50 shore A.

According to another aspect of the invention, a ureteral stent for placement in a bladder, a kidney and a ureteral passageway connecting the bladder and kidney for allowing urine and/or stones to flow from the kidney to the bladder and not from the bladder to the kidney is provided. The ureteral stent includes a resilient bladder portion configured to be positioned in the bladder, the bladder portion being biased in an unrestrained position, a kidney portion having a resilient fixing portion configured to be positioned in the kidney and a ureter portion configured to be positioned in the kidney and the ureteral passageway, the resilient fixing portion being biased in an unrestrained position, and one or more threads connecting the bladder portion and the ureter portion.

The one or more threads is a suture.

According to still another aspect of the invention, a method for forming a ureteral stent having a bladder portion, a kidney portion, and a tether extending therebetween is provided. The method includes extruding the stent to form a flexible tubular member, removing a section of the tubular member to form the tether, modifying the bladder portion to form a resilient fixing portion biased in an unrestrained position, and modifying the kidney portion to form a resilient fixing portion biased in an unrestrained position.

The foregoing and other features of the invention are hereinafter described in greater detail with reference to the accompanying drawings.

DETAILED DESCRIPTION

The principles of the present application have particular application to ureteral stents for unblocking a ureteral passageway and thus will be described below chiefly in this context. It will, of course, be appreciated and also understood that the principles of the application may be useful in other medical applications, such as other stent applications, for example biliary stents.

Figure 1:
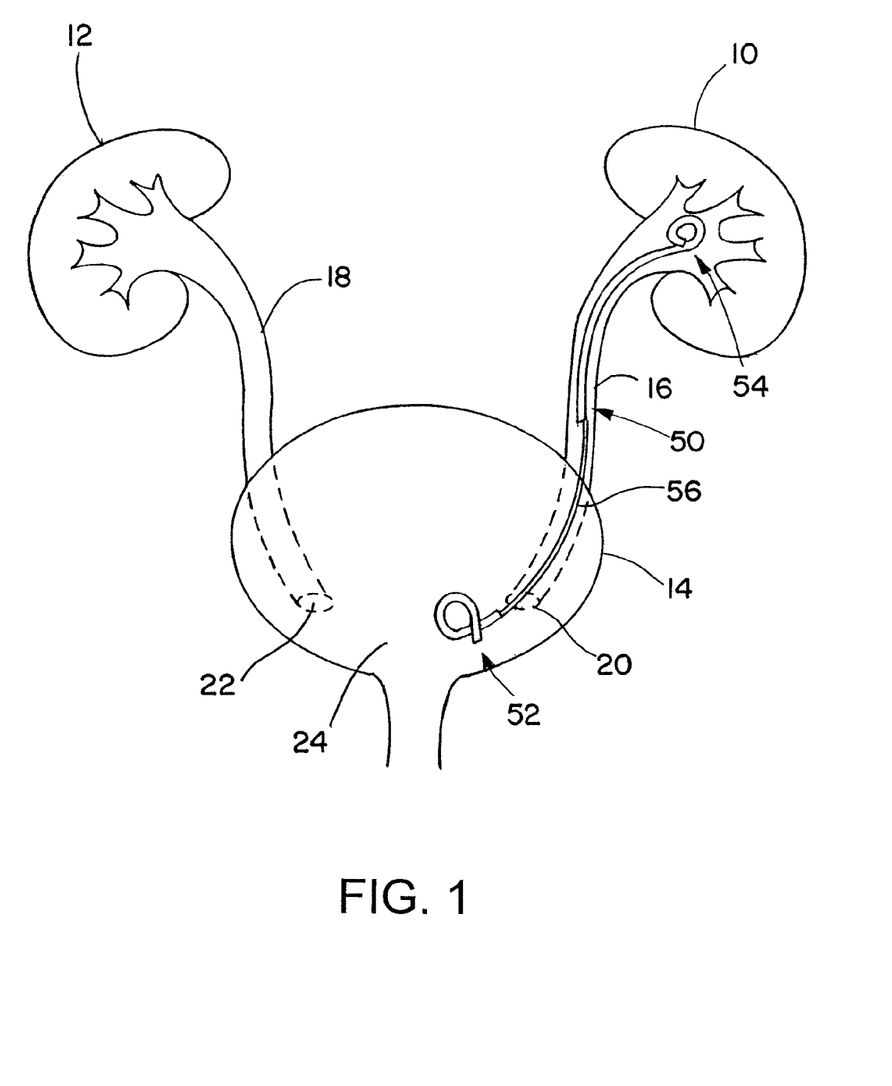
FIG. 1 is a schematic view of an exemplary stent according to the invention positioned in a patient.

Referring now in detail to the drawings and initially to FIG. 1, a pair of kidneys 10 and 12 and a bladder 14 of a patient are shown. The kidneys 10 and 12 are connected to the bladder 14 by respective ureteral passageways 16 and 18. The ureteral passageways 16 and 18 each include a portion extending into the bladder 14 that moves from an uncompressed state to compressed state and in a normal state only allows urine to pass from the kidneys 10 and 12 to the bladder 14 with the help of peristalsis of the ureter. When one of the passageways 16 and 18 becomes blocked, for example by swelling near one of the kidneys 10 and 12 or blockage from a kidney or ureteral stone, a ureteral stent may be positioned in the kidney 10, 12, ureteral passageway 16, 18 and bladder 14 to assist in opening the passageway 16, 18 to aid in the flow of urine.

The ureteral stent may be formed by a tube extending from the kidney 10, 12 to the bladder 14, the tube having a first helical end positioned in the kidney and a second helical end positioned in the bladder. Although such a stent allows urine to flow through and around the tube into the bladder, the tube may cause or contribute to patient discomfort and further medical problems. For example, the tube causes ureter orifices 20 and 22, which normally move from a compressed state to an uncompressed state, to remain open at all times allowing urine to flow from the bladder 14 to the kidney 10, 12 and the kidney 10, 12 to the bladder 14. Keeping the ureter orifices 20 and 22 open, thereby preventing the orifices 20 and 22 from compressing to prevent urine from flowing from the bladder 14 to the kidneys 10 and 12, may lead to urinary reflux and flank pain, for example. The bladder end of the ureteral stent also can migrate over time such that it rests on or bangs against a trigone muscle 24 of the patient or wall of the bladder 14, causing blood in the urine, a continual urge to urinate, and bladder spasms resulting from stent pain and therefore increased discomfort of the patient.

Figure 2:
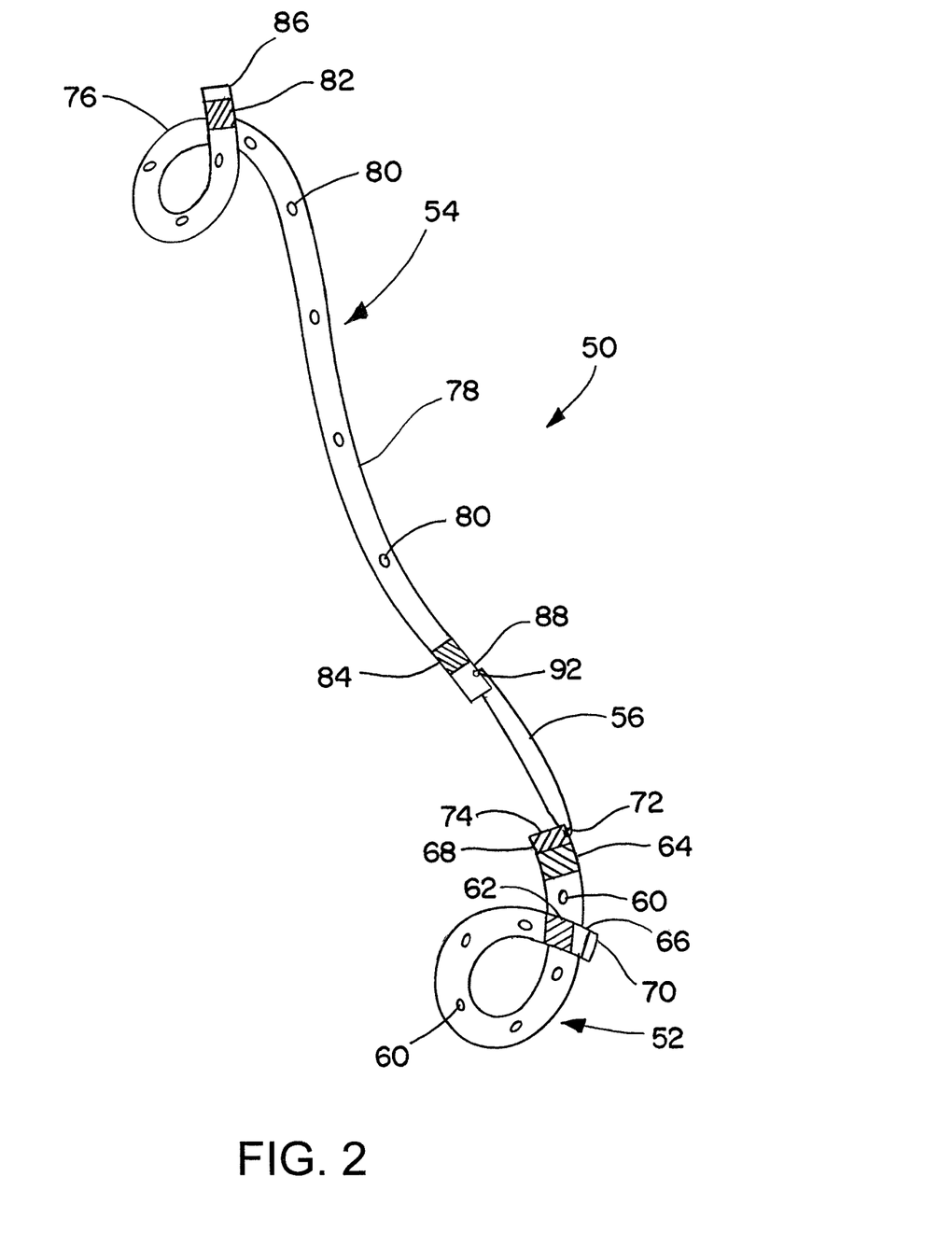
FIG. 2 is a schematic view of the exemplary stent of FIG. 1.

To minimize the footprint of the stent in the bladder 14 and/or near the ureteral orifices 20 and 22 and to allow urine to flow in a single direction from the kidneys 10 and 12 to the bladder 14 and not from the bladder 14 to the kidneys 10 and 12, thereby reducing the adverse affects associated with stents, an exemplary ureteral stent 50 is provided. As shown in FIGS. 1 and 2, the stent 50 includes a bladder portion 52 positioned in the bladder 14, a kidney portion 54 positioned in the kidney 10 and ureteral passageway 16, and one or more tethers 56 coupling the bladder portion 52 to the kidney portion 54. The tether 56 may be a suitable thread, which is not limited to fibers, and may include, for example, a wire, such as a thin wire. Although not shown, it will be appreciated that the stent 50 may additionally or alternatively be positioned in the kidney 12 and ureteral passageway 18.

The bladder portion 52 is a resilient fixing member having any suitable shape, such as a tube that is curved in a flexible loop as shown in FIG. 2 when unrestrained to prevent the bladder portion 52 from migrating into the ureteral passageway 16. The bladder portion 52 is in an unrestrained shape when positioned in the bladder 14, and in a restrained shape, such as a substantially straight shape, when being positioned in the bladder 14. It will be appreciated that the bladder portion may be any suitable shape when unrestrained, such as J-shaped (FIG. 3), helical (FIGS. 4 and 5), t-bar (FIG. 6), triangular (FIG. 9), circular (FIG. 10), etc. It will also be appreciated that the bladder portion may be made of any suitable material that does not irritate the patient's ureter tissue, such as urethane polymer, silicone, a thermoplastic, for example a thermoplastic polymer or elastomer, etc. It will also be appreciated that the suitable material may be a buoyant material to allow the bladder portion to float in the bladder, for example when the bladder is filled with urine, to allow the bladder portion to float off the trigone thereby decreasing irritation.

The bladder portion 52 may include one or more openings 60 in a wall of the bladder portion that allow fluid to flow in/out of the bladder portion. The openings may be any suitable shape and size, such as a spiral, a circular opening, etc. The bladder portion 52 may also include at least one radiopaque element, such as a radiopaque band, and in the illustrated embodiment radiopaque bands 62 and 64 near first and second ends 66 and 68 of the bladder portion, respectively. The radiopaque bands may be any suitable radiopaque element provided to assist an operator in placing the stent 50. Additionally or alternatively, it will be appreciated that the bladder portion 52 may be radiopaque to assist in positioning the stent. The bladder portion may also include a tip or ring 70 at the first end 66 having a stiffness greater than a stiffness of the rest of the bladder portion 52 to assist in the positioning of the stent 50.

Similar to the bladder portion 52, the kidney portion 54 has a resilient fixing portion 76, such as a tube in the form of a flexible loop when unrestrained to secure the kidney portion in the kidney 10. The resilient fixing portion 76 is in an unrestrained shape when positioned in the kidney, and in a restrained shape, such as a substantially straight shape, when being positioned in the kidney. It will be appreciated that the fixing portion may be any suitable shape when unrestrained, such as J-shaped (FIG. 3), helical (FIGS. 4 and 5), etc. It will also be appreciated that the bladder portion 52 and kidney portion 54 may have the same or different shapes when unrestrained, for example the bladder portion 52 and kidney portion 54 may both be a flexible loop as shown in FIG. 2, the bladder portion 52 or kidney portion 54 may be J-shaped and the other portion may be helical, etc.

The kidney portion 54 may be made of any suitable material that does not irritate the patient's ureter tissue, such as urethane polymer, silicone, a thermoplastic, for example a thermoplastic polymer or elastomer, etc. It will be appreciated that the kidney portion and bladder portion may be made of the same or different materials having the same or different durometers that are sufficient to allow for delivery reliability during placement while having tensile properties allowing for removal from the body. The kidney portion may have a durometer, for example, of 50 to 80 shore A and preferably 50 to 60 shore A, and the bladder portion may have a durometer, for example, of 25 to 50 shore A, and preferably 30 to 40 shore A. It will also be appreciated that the kidney portion, bladder portion, and/or tether may be made of one or more of an absorbable or non-absorbable material, a material to prevent calcification, a material to prevent incrustation, and may additionally or alternatively be impregnated with a suitable antibiotic and/or be drug-eluting.

In an embodiment, the bladder portion 52 has a softer durometer than the kidney portion 54 so that the bladder portion 52 is compliant with bladder contractions and to reduce irritation to the trigone muscle 24. Additionally or alternatively, the resilient fixing portion 76 of the kidney portion 54 is harder than a ureter portion 78 of the kidney portion 54. For example, the kidney portion 54 may have transition zones along its length going from a harder durometer at the fixing portion 76 to a softer durometer at the end of the ureter portion 78. It will also be appreciated that the bladder portion 52 and/or kidney portion 54 may be heat activated such that the portions are stiffer during placement and soften after placement in the body.

Referring again to the kidney portion 54, the kidney portion has the ureter portion 78, which may be a flexible tubular portion, configured to extend from the resilient fixing portion 76 in the kidney 10 into the ureteral passageway 16 to keep the passageway open, for example when there is swelling between the kidney 10 and passageway 16. The kidney portion 54 may also include one or more openings 80 in a wall of the kidney portion 54 that allow fluid to flow in/out of the kidney portion 54. The openings may be any suitable shape and size, such as a spiral (FIG. 3), a circular opening, etc.

The kidney portion 54 also includes at least one radiopaque element, such as a radiopaque band, and in the illustrated embodiment radiopaque bands 82 and 84 near first and second ends 86 and 88 of the kidney portion 54, respectively, although it will be appreciated that the kidney portion 54 may additionally or alternatively be radiopaque to assist in placing the stent. It will also be appreciated that the bladder portion 52 and/or kidney portion 54 may include measurement markers along their respective lengths to assist in positioning the stent 50.

As noted above, the bladder portion 52 and kidney portion 54 are coupled together by one or more tethers 56. The tethers 56 have a thin flexible cross-section such that a transmural portion of the ureteral passageway, which passes through the bladder wall starting at the ureter opening and continuing through the thickness of the bladder 14, can clamp or remain in its normal state around the tethers 56. This allows for the single direction of urine flow from the kidney 10 to the bladder 14 to be maintained and prevents the flow or reflux of urine from the bladder 14 to the kidney 10. The tethers 56 may be any suitable tether having any suitable cross-sectional shape, such as a suitable suture made of cotton, a polymer such as nylon, etc. The tethers may also be any suitable length. For example, the tethers may be uniform in length for patients of varying sizes and the ureter portion 78 may be altered in length to accommodate patients of varying sizes and/or the suture lengths may be varied for patients of varying sizes. It will also be appreciated that the one or more tethers 56 may include one or more radiopaque marks along their lengths.

The tethers 56 are coupled to the second end 68 of the bladder portion and the second end 88 of the kidney portion in any suitable manner, for example by adhesive, knotting, etc. For example, as shown in FIG. 2, the tether 56 has an end received in an opening 92 at the second end 88 of the kidney portion 54 such that a portion of the tether 56 is outside the kidney portion 54 and a portion is inside the kidney portion 54. The portion of the tether 56 inside the kidney portion 54 extends to an inside of the bladder portion 52, where the tether extends out of an opening 72 in the bladder portion 52. Ends of the tether 56 are coupled together outside the bladder portion or the kidney portion, for example by tying the two ends together forming a knot. The excess tether created by the tying may then be cut off.

In an embodiment, a sleeve 74, such as a heat shrink, tape, UV adhesive, etc., is coupled to the second end 68 of the bladder portion to hold down the knot and excess tether to prevent or minimize irritation to the patient. It will be appreciated that by using the sleeve 74, the excess tether can be left longer than without the use of a sleeve 74 allowing the tether to lie down, reducing the thickness of the bladder portion 52. It will also be appreciated that the sleeve 74 may have radiopaque material on an external surface thereof to either replace the radiopaque band 64 or be used in conjunction with the band. Alternatively, the radiopaque band 64 may be positioned over the sleeve 74 or knot. The sleeve 74 is provided on the kidney portion 54 and/or the bladder portion 52 to cover knots on the outside of the kidney and/or bladder portion. It will be appreciated, however, that a stent may be provided having knots on the inside of the bladder portion and/or the kidney portion, in which case the sleeve may be omitted.

When the stent 50 is positioned in the body of the patient, the one or more tethers 56 extend from the ureteral passageway 16, through the ureter orifice 20 and into the bladder 14. The one or more tethers 56 allow the bladder portion 52 to anchor the kidney portion 54 to keep the ureter portion 78 in position in the ureteral passageway 16, for example to prevent the ureter portion 78 from curling up. The tether also allows the ureter orifice 20 to freely move between the compressed state and the uncompressed state to allow the ureter orifice to move to the compressed state when the bladder fills, thereby preventing urine from moving backwards. The tether also allows urine to pass in its normal direction from the kidney to the bladder. In this way, the tether prevents or minimizes urinary reflux, flank pain, patient discomfort, etc.

The one or more tethers 56 additionally allow the bladder portion 52 to move freely in the bladder 14, for example as the bladder fills with urine, to prevent the bladder portion 54 from irritating the trigone muscle; to prevent or minimize bladder spasms, blood in the urine and a constant urge to urinate; and to avoid a rigid positioning of the stent that would hold the stent in one position over the trigone. The bladder portion thereby freely floats and/or dangles within the bladder, i.e. not held in a rigid position, and is constrained only by the length of the tether.

When being positioned, the kidney portion 54 and the bladder portion 52 are restrained, i.e. substantially straightened, to allow the portions to be navigated through the patient. It should be appreciated that for purposes of positioning, at least the ureter portion 78 of the kidney portion 54 has an inner diameter that is less than an inner diameter of the bladder portion 52. Once the kidney portion 54 is positioned and a guidewire withdrawn, the kidney portion moves to its unrestrained shape where the resilient fixing portion 76 is secured in the kidney 10 and the ureter portion 78 extends from the kidney 10 into the ureteral passageway 16 to keep the passageway open near the kidney. Similarly, once the bladder portion 52 is positioned and the guidewire withdrawn, the bladder portion 52 moves to its unrestrained shape where the bladder portion 52 anchors the ureter portion 78 while allowing the ureter orifice 20 to freely move between the compressed state and uncompressed state.

Turning now to FIGS. 3-10, exemplary embodiments of the ureteral stent is shown at 150, 250, 350, 450, 550, 650, 750 and 850. The ureteral stents 150, 250, 350, 450, 550, 650, 750 and 850 are substantially the same as the above-referenced ureteral stent 50, and consequently the same reference numerals but indexed by 100, 200, 300, 400, 500, 600, 700 and 800 respectively are used to denote structures corresponding to similar structures in the stents. In addition, the foregoing description of the stent 50 is equally applicable to the stent 150, 250, 350, 450, 550, 650, 750 and 850 except as noted below. Moreover, it will be appreciated upon reading and understanding the specification that aspects of the stents may be substituted for one another or used in conjunction with one another where applicable.

Figure 3:
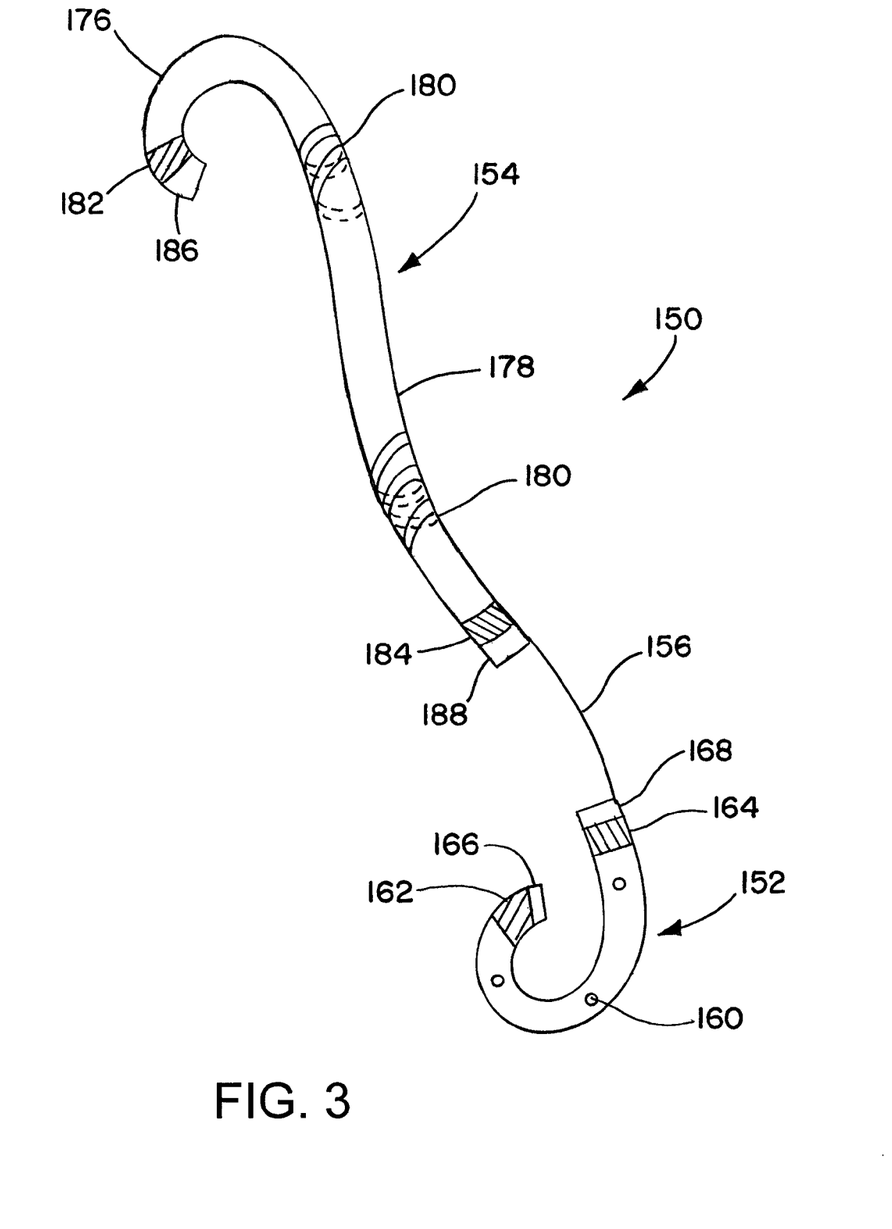
FIG. 3 is a schematic view of another exemplary stent according to the invention.

Referring now to FIG. 3, the bladder portion 152 is a J-shaped flexible tube when unrestrained that prevents the bladder portion 152 from migrating into the ureteral passageway 16. Similarly, the fixing portion 176 of the kidney portion 154 is a J-shaped flexible tube when unrestrained to secure the kidney portion in the kidney 10. The second end 168 of the bladder portion 152 and the second end 188 of the kidney portion 154 are each coupled to a tether 156 in any suitable manner. The kidney portion 154 includes one or more spiral openings 180 extending through the wall of the kidney portion and the bladder portion 152 includes one or more circular openings 160 extending through the wall of the bladder portion to allow fluid to flow in/out of the kidney portion 154 and bladder portion 152. It will be appreciated that the bladder portion 152 may additionally or alternatively include one or more spiral openings extending through the wall of the bladder portion and the kidney portion 154 may additionally or alternatively include one or more circular openings extending through the wall of the kidney portion.

The kidney portion 154 has a diameter near the first end 186 that is larger than the diameter at the second end 188. For example, the diameter of the kidney portion may gradually taper down from the first end 186 to the second end 188. It will also be appreciated that the bladder portion 154 may have a diameter at the second end 168 that is larger than the diameter at the first end 166 of the bladder portion 152. Additionally, the diameter at the second end 168 of the bladder portion 152 may be substantially equal to or less than the diameter of the kidney portion at the second end 188, and the diameter at the first end 166 less than the diameter at the second end 168. Such a stent may be used as an endopyelotomy stent, providing a large diameter near the kidney for ureteral healing and a smaller diameter in the bladder for patient comfort.

Figure 4:
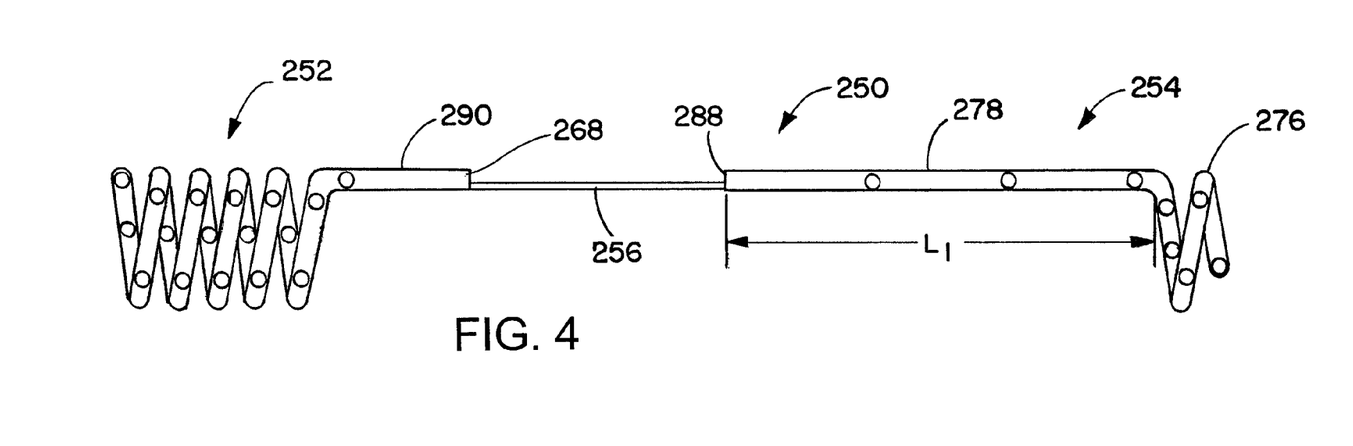
FIG. 4 is a schematic view of yet another exemplary stent according to the invention.
Figure 5:
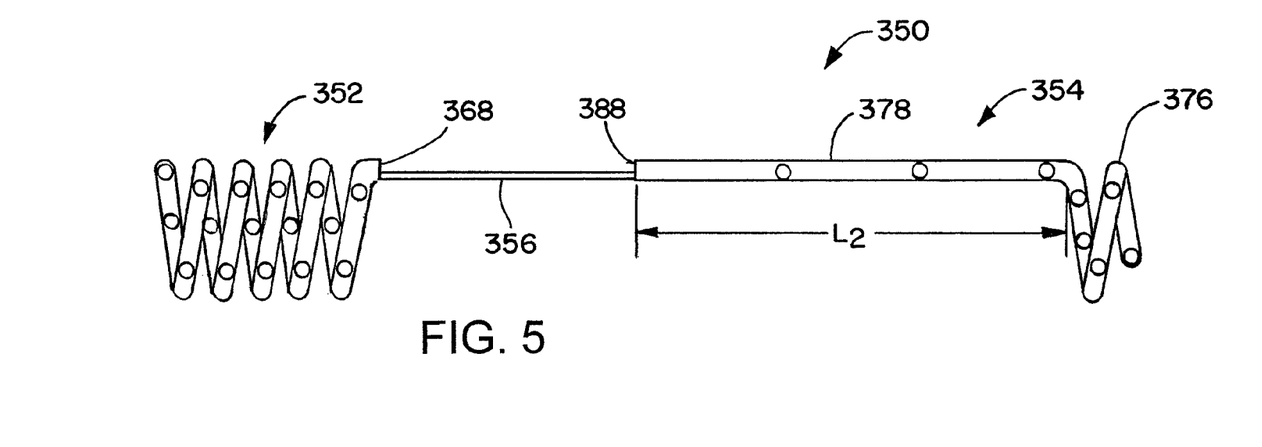
FIG. 5 is a schematic view of still another exemplary stent according to the invention.

Referring now to FIGS. 4 and 5, the bladder portions 252 and 352 are helical flexible tubes when unrestrained that prevent the bladder portions 252 and 352 from migrating into the ureteral passageway. Similarly, the fixing portions 276 and 376 of the kidney portions 254 and 354 are helical flexible tubes when unrestrained to secure the kidney portions in the kidney. The helical flexible tube portions 252, 352, 276, 376 of the bladder portions 252 and 352 and kidney portions 254 and 354 may have any suitable number of coils. The second ends 268 and 368 of the bladder portions 252 and 352 and the second ends 288 and 388 of the kidney portions 254 and 354 are each coupled to a respective tether 256, 356 in any suitable manner, such as by an adhesive that is covered by a sleeve.

The ureter portions 278 and 378 of the kidney portions 254 and 354 have varying lengths for use with patients having ureteral passageways of varying sizes, such as pediatric lengths and sizes, adult lengths and sizes, etc. As shown, the ureter portion 278 has a length L1 for use with a patient having a ureteral passageway of a first length, and the ureter portion 378 has a length L2, which is greater than the length L1, for use with a patient having a ureteral passageway of a second length greater than the first length. Additionally, the bladder portion 252 includes a substantially straightened portion 290 that is coupled to the tether, while the bladder portion 352 is formed without a straightened portion. It will be appreciated that the substantially straightened portion 290 may be included in the bladder portion 352 and not included in the bladder portion 252.

Figures 6, 6A:
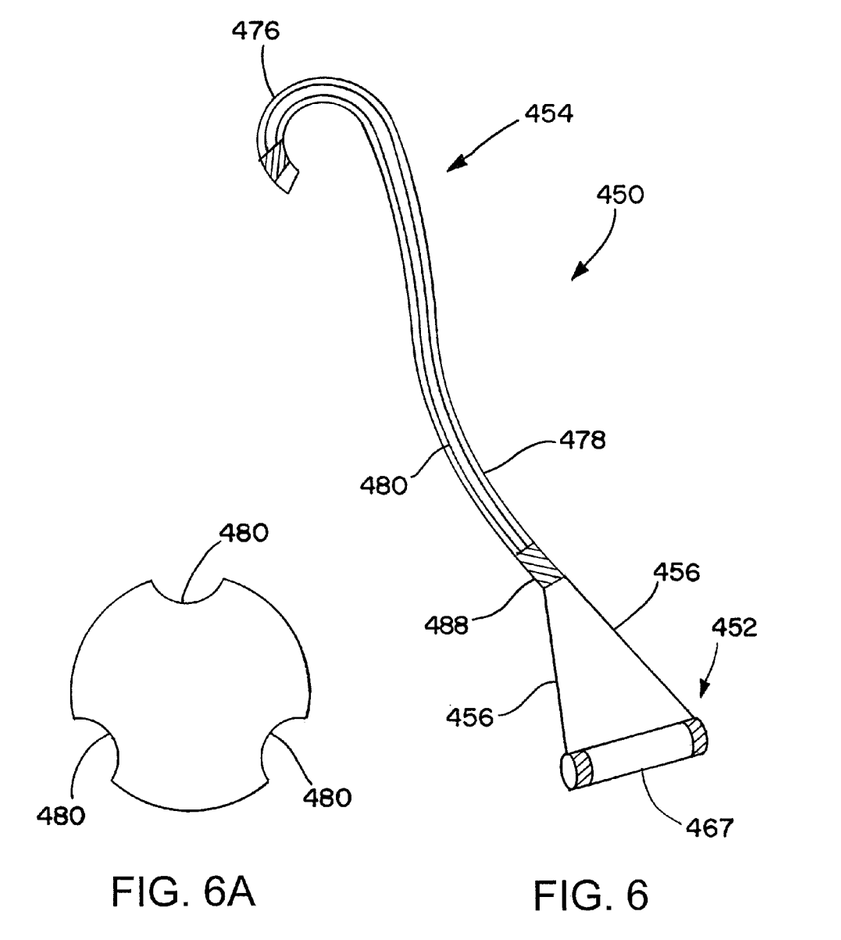
FIG. 6 is a schematic view of a further exemplary stent according to the invention.
FIG. 6A is a top view of a kidney portion of the stent of FIG. 6.

Referring now to FIG. 6, the bladder portion 452 is a t-bar that prevents the bladder portion 452 from migrating into the ureteral passageway. The kidney portion 454 is shown as a J-shaped flexible tube, although it will be appreciated the kidney portion may have any suitable shape as discussed above. Ends of a tubular portion 467 of the t-bar and the second end 488 of the kidney portion 454 are coupled to two suitable tethers in any suitable manner, for example, by knots on the outside of the t-bar and/or ureter portion 478 that are covered by a sleeve as discussed above or by knots on an inside of the ends of the tubular portion 467 and/or ureter portion 478.

The bladder portion 452 and/or kidney portion 454 may include one or more channels 480 along the length thereof that are provided to guide fluid, such as urine, out of the kidney 10 and into the bladder 14. For example, FIG. 6A shows a top view of the kidney portion 454 including three channels 480 that are circumferentially spaced around the kidney portion 454. The channels 480 may be evenly circumferentially spaced around the kidney portion 454 or spaced in any other suitable manner.

Figure 7:
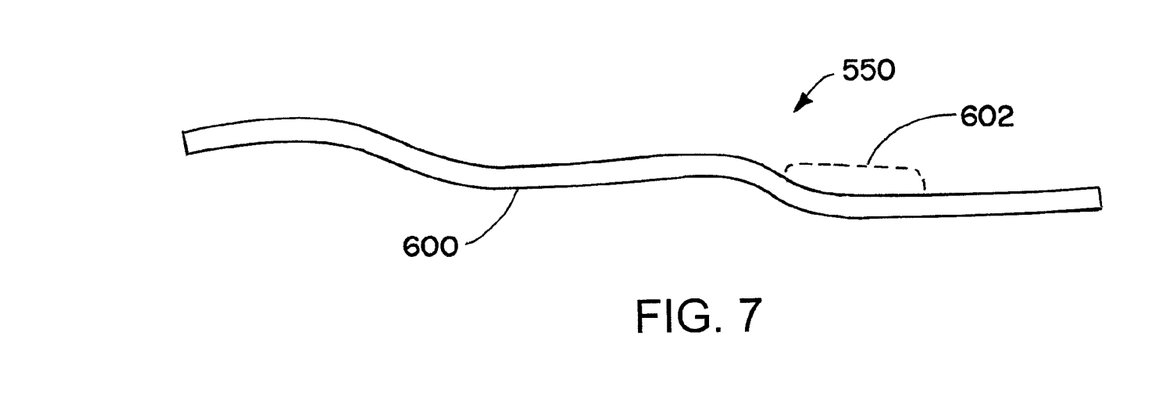
FIGS. 7 and 8 are schematic views of still a further exemplary stent according to the invention.
Figure 8:
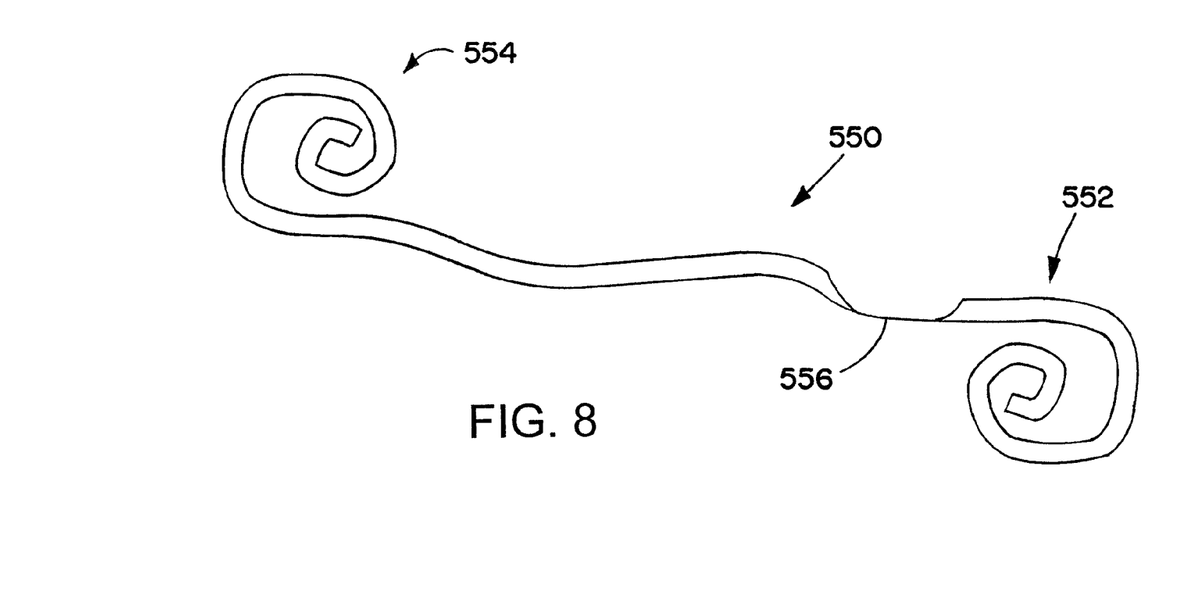

Referring now to FIGS. 7 and 8, the stent 550 is formed by extruding the stent to form a flexible tubular member 600. Then at region 602, a section of the tubular member 600 is removed to form the tether 556. Before or after removing the section at region 602, geometric modifications, such as forming the fixing elements 552 and 554, adding retention notches, openings, etc. may be performed, for example by heat-forming, and surface edge softening may be performed.

Figure 9:
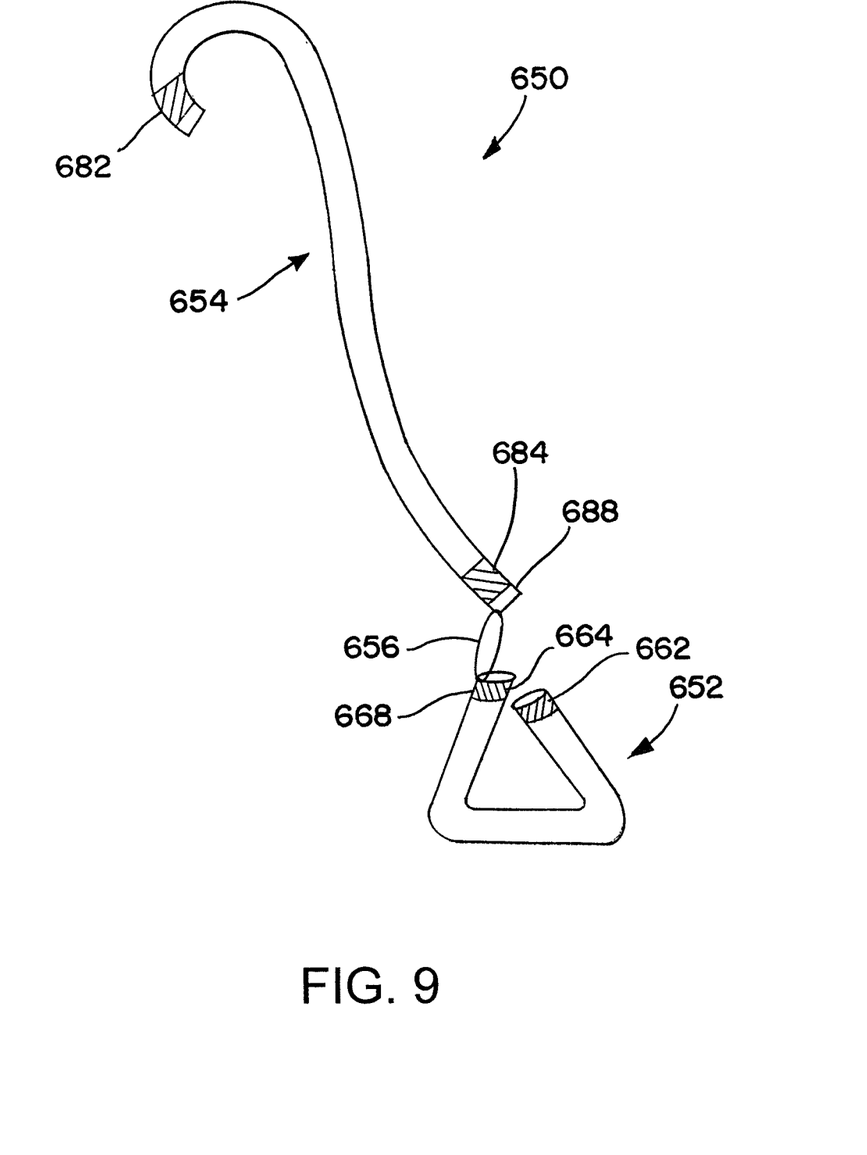
FIG. 9 is a schematic view of yet another exemplary stent according to the invention.

Referring now to FIG. 9, the kidney portion 654 is a J-shaped flexible tube when unrestrained that secures the kidney portion 654 in the kidney 10. The bladder portion 652 is substantially triangular when unrestrained to prevent the bladder portion 652 from migrating into the ureteral passageway 16. The second end 668 of the bladder portion 652 and the second end 688 of the kidney portion 654 are each coupled to a tether 656 in any suitable manner. During positioning, the substantially triangular bladder portion is substantially straightened.

Figure 10:
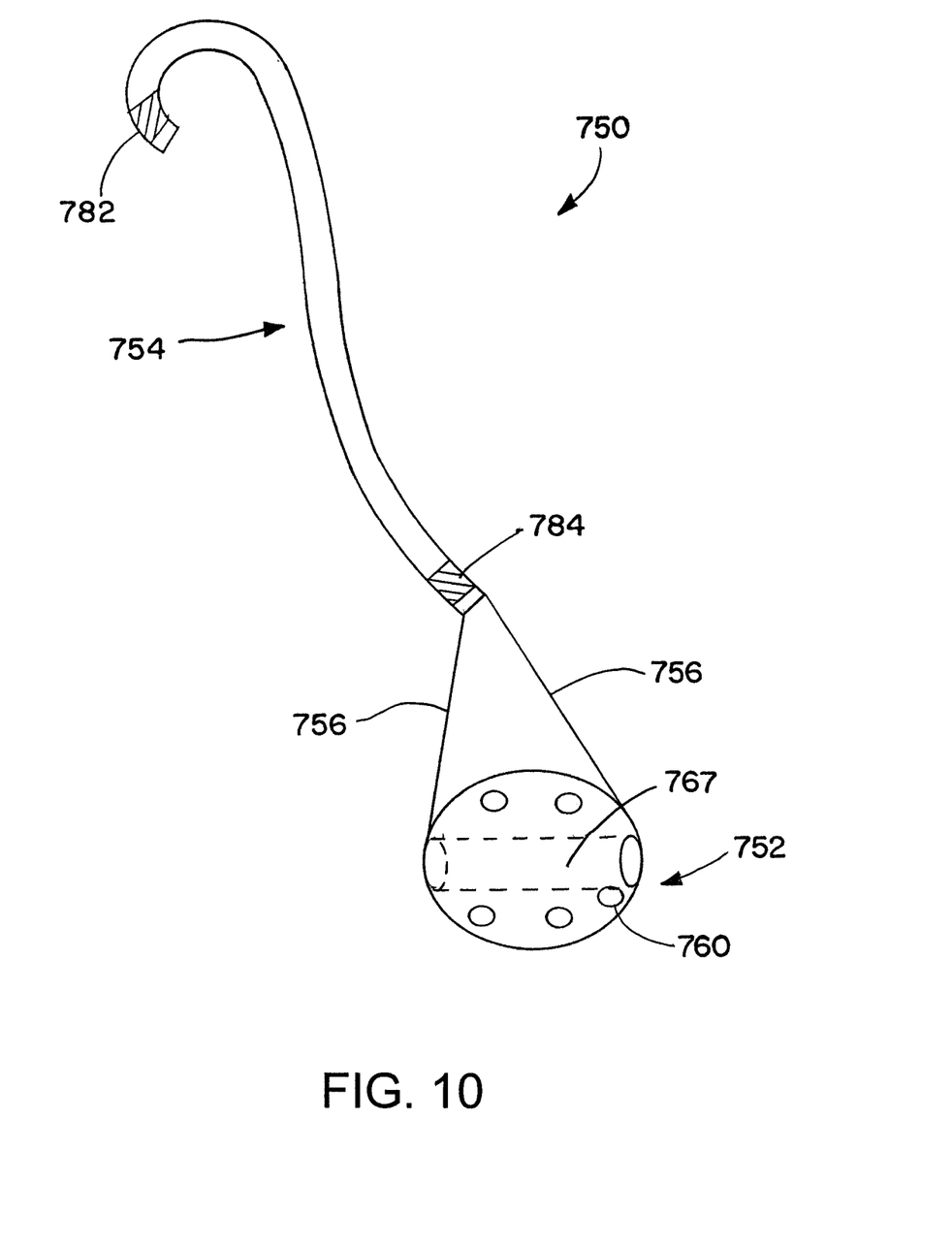
FIG. 10 is a schematic view of a further exemplary stent according to the invention.

Referring now to FIG. 10, the kidney portion 754 is a J-shaped flexible tube when unrestrained that secures the kidney portion 754 in the kidney 10. The bladder portion 752 is substantially circular and sized to be larger than the ureter orifice 20 to prevent the bladder portion 752 from migrating into the ureteral passageway 16. The bladder portion 752 includes a through-hole 767 extending therethrough and one or more openings 760 extending through the bladder portion. The bladder portion may also include a seat at one end of the through-hole 767 for an end of a pusher to seat against during placement.

Figure 11:
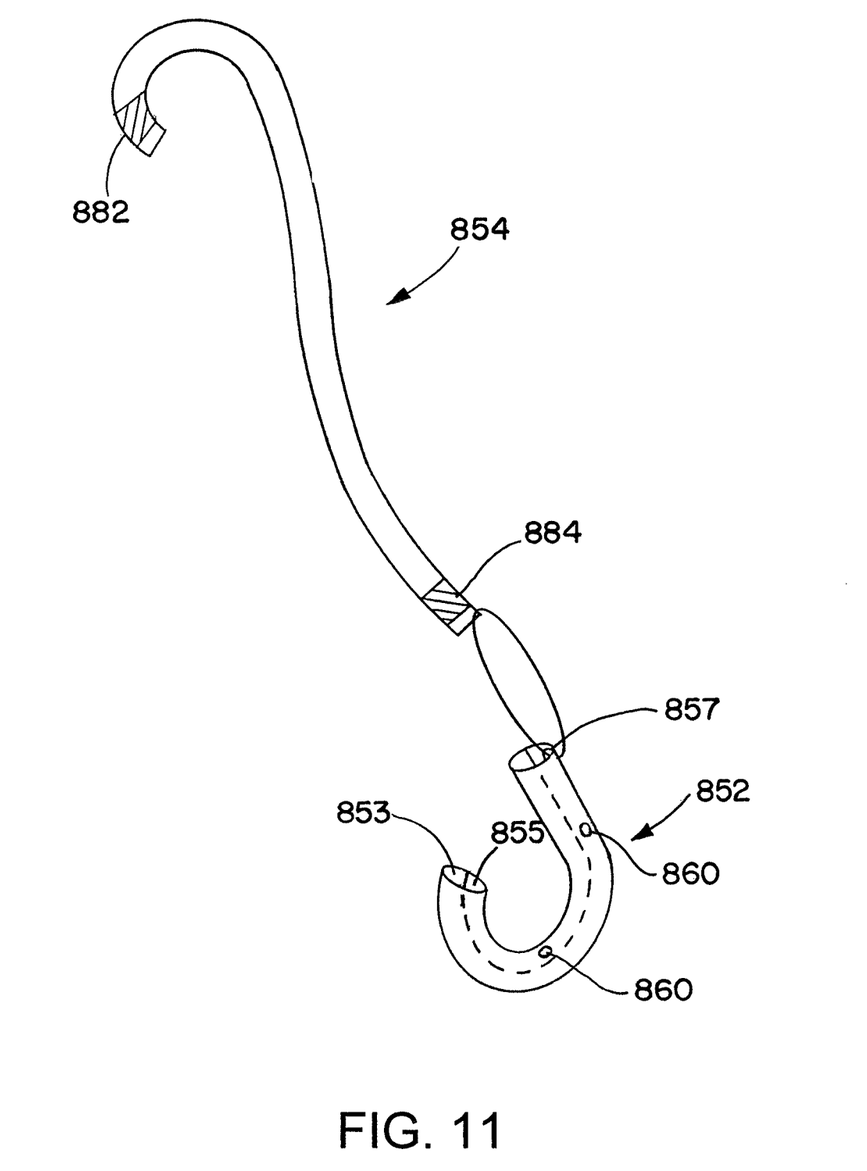
FIG. 11 is a schematic view of a yet further exemplary stent according to the invention.

Referring now to FIG. 11, the kidney portion 854 is a J-shaped flexible tube when unrestrained that secures the kidney portion 854 in the kidney 10. Similarly, the bladder portion 852 is a J-shaped flexible tube when unrestrained that prevents the bladder portion 852 from migrating into the ureteral passageway 16. The bladder portion 852 includes a first lumen 853 for the knot 857 to be disposed to prevent the knot from irritating the trigone area, for example, and a second lumen 855 for receiving a stent pusher assembly and guidewire. One or more openings 860 may be provided in the first and/or second lumens that allow fluid to flow in/out of the bladder portion. Similarly, the kidney portion may include a first lumen for a knot to be disposed and a second lumen for receiving a guidewire.

The above-described ureteral stents may be positioned in the kidney 10 and bladder 14 using any suitable stent pusher assembly, such as the type disclosed in U.S. Patent Application No. 61/657,238, which is hereby incorporated herein by reference.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A ureteral stent for placement in a bladder, a kidney and a ureteral passageway connecting the bladder and the kidney, the ureteral stent including:
   a bladder portion configured to be positioned in the bladder, the bladder portion being resilient and biased in an unrestrained position to prevent the bladder portion from migrating into the ureteral passageway when positioned in the bladder;
   a kidney portion configured to be positioned in the kidney and the ureteral passageway, the kidney portion being tubular and defining a tubular ureter portion configured to be positioned in the kidney and the ureteral passageway to place the ureteral passageway in an open state and a tubular resilient fixing portion biased in an unrestrained position to secure the resilient fixing portion in the kidney when positioned in the kidney;
   a tether connecting the bladder portion and the ureter portion to allow the bladder portion to float in the bladder and to allow a ureter orifice connecting the ureteral passageway to the bladder to move between a compressed state and an uncompressed state, wherein the tether has first and second ends knotted together outside the bladder and kidney portions forming a knotted portion; and
   a sleeve coupled to a wall of the ureter portion that covers the knotted portion to prevent the knotted portion from irritating the ureter, the sleeve having a length less than a length of the ureter portion.

2. The ureteral stent according to claim 1, wherein the bladder portion and the fixing portion are movable between respective restrained positions when being positioned in the bladder and kidney, respectively, and the respective unrestrained positions when positioned in the bladder and kidney, respectively.

3. The ureteral stent according to claim 2, wherein the bladder portion and kidney portion are substantially straight when in the respective restrained positions and curved when in the respective unrestrained positions.

4. The ureteral stent according to claim 1, wherein the bladder portion and kidney portion each include at least one radiopaque element on outer surfaces thereof to assist an operator in positioning the stent.

5. The ureteral stent according to claim 4, wherein the bladder portion and kidney portion have first and second ends, respectively, each end having at least one radiopaque element.

6. The ureteral stent according to claim 1, wherein the bladder portion includes a tip at a first end opposite a second end coupled to the tether, the tip having a stiffness greater than a stiffness of a remaining portion of the bladder portion.

7. The ureteral stent according to claim 1, wherein the bladder portion and ureter portion of the kidney portion each include a least one opening in a wall thereof providing a passage between an outside of the bladder and kidney portions and an inside of the bladder and kidney portions for receiving the tether, wherein the tether extends from the inside of the bladder and kidney portions to the outside of the bladder and kidney portions, and wherein the tether has a first end and a second end coupled together outside the bladder and kidney portions forming a coupled tether portion.

8. The ureteral stent according to claim 1, wherein the tether is a suture.

9. The ureteral stent according to claim 1, wherein the bladder portion and the fixing portion are a flexible loop when in their unrestrained positions.

10. The ureteral stent according to claim 1, wherein the bladder portion and the fixing portion are J-shaped when in their unrestrained positions.

11. The ureteral stent according to claim 1, wherein the bladder portion and the fixing portion are helical when in their unrestrained positions.

12. The ureteral stent according to claim 1, wherein the kidney portion has a durometer between 50 shore A and 80 shore A.

13. The ureteral stent according to claim 1, wherein the resilient fixing portion has a durometer greater than a durometer of the ureter portion.

14. The ureteral stent according to claim 1, wherein the bladder portion has a durometer between 25 shore A and 50 shore A.

15. The ureteral stent according to claim 1, wherein the kidney portion has transition zones along its length going from a harder durometer at the resilient fixing portion to a softer durometer at an end of the ureter portion connected to the tether.

16. A ureteral stent for placement in a bladder, a kidney and a ureteral passageway connecting the bladder and kidney, the ureteral stent including:

a bladder portion configured to be positioned in the bladder, the bladder portion being resilient and biased in an unrestrained position to prevent the bladder portion from migrating into the ureteral passageway when positioned in the bladder;

a kidney portion configured to be positioned in the kidney and the ureteral passageway, the kidney portion having a ureter portion configured to be positioned in the kidney and the ureteral passageway to place the ureteral passageway in an open state and a resilient fixing portion biased in an unrestrained position to secure the resilient fixing portion in the kidney when positioned in the kidney;

at least one tether connected to the bladder portion and the ureter portion to allow the bladder portion to float in the bladder and to allow a ureter orifice connecting the ureteral passageway to the bladder to move between a compressed state and an uncompressed state, wherein the tether has a length and first and second ends at opposite ends of the length from one another, and wherein the first and second ends are knotted together outside the bladder and kidney portions forming a knotted portion; and a sleeve coupled to the wall of the ureter portion that covers the knotted portion to hold down the knotted portion and part of the tether to prevent the knotted portion from irritating a patient and to allow the tether to lie down to reduce a thickness of the ureter portion, the sleeve having a length less than a length of the ureter portion.

* * * * *